US00PP24244P2

(12) United States Plant Patent
Hurd

(10) Patent No.: US PP24,244 P2
(45) Date of Patent: Feb. 11, 2014

(54) *MONARDA* PLANT NAMED 'PARDON MY PINK'

(50) Latin Name: *Monarda didyma*
Varietal Denomination: Pardon My Pink

(75) Inventor: Kevin A. Hurd, Chicago, IL (US)

(73) Assignee: Walters Gardens Inc, Zeeland, MI (US)

( * ) Notice: Subject to any disclaimer, the term of this patent is extended or adjusted under 35 U.S.C. 154(b) by 98 days.

(21) Appl. No.: 13/506,516

(22) Filed: Apr. 24, 2012

(51) Int. Cl.
*A01H 5/00* (2006.01)

(52) U.S. Cl.
USPC ..... Plt./455

(58) Field of Classification Search
USPC ..... Plt./455
See application file for complete search history.

*Primary Examiner* — Susan McCormick Ewoldt

(57) ABSTRACT

The new and distinct cultivar of ornamental cultivar of ornamental Bee Balm named *Monarda didyma* 'Pardon My Pink' has very short, compact, branching stems, medium to dark green foliage, numerous medium fuchsia-pink flowers and resistance to powdery mildew.

1 Drawing Sheet

Botanical classification: *Monarda didyma.*
Variety denomination: 'Pardon My Pink'.

BACKGROUND OF THE INVENTION

The present invention relates to the new and distinct cultivar of Bee Balm, botanically known as *Monarda didyma* 'Pardon My Pink', and hereinafter also referred to solely as the cultivar 'Pardon My Pink' or the "new plant". The new plant was hybridized in July of 2006 and separated out for further evaluation in the summer of 2007 by Kevin A. Hurd in the trial gardens fields of a Zeeland, Mich., USA, as a planned linear hybrid cross #06-01 between *Monarda didyma* 'ACrade' U.S. Plant Pat. No. 19,580 more commonly known as 'Grand Parade' as the female or seed parent and *Monarda didyma* 'AChall' U.S. Plant Pat. No. 19,582 more commonly known as 'Grand Marshall' as the male or pollen parent. The plant has been asexually propagated by stem cuttings at the same nursery in the greenhouses in Zeeland, Mich., and the subsequent asexually propagated plants found to be stable and identical to the original selection.

BRIEF SUMMARY OF THE PLANT

*Monarda didyma* 'Pardon My Pink' is unique from its parents and all other Bee Balm plants known to the inventor. The nearest comparison varieties are the two parents, 'Pardon My Purple' U.S. Plant Pat. No. 22,170, 'Pink Supreme' U.S. Plant Pat. No. 14,204 and 'Pink Lace' U.S. Plant Pat. No. 18,367. 'Pink Supreme', 'Pink Lace' and 'Grand Marshall' are all redder in flower color. 'Grand Parade' is more violet, and along with 'Pardon My Purple' and 'Grand Marshall' are all much darker in flower pigment. Height-wise, 'Pink Supreme' is about 60 cm, 'Pink Lace' and 'Grand Marshall' about 45 cm, 'Grand Parade' about 40 cm and 'Pardon My Purple' about 30 cm while 'Pardon My Pink' is about 28 cm tall in flower.

The following are traits of *Monarda didyma* 'Pardon My Pink' that in combination distinguish it from all other Bee Balm known to the inventor:

1. Very short, winter-hardy, clumping habit.
2. Medium to dark-green powdery mildew resistant foliage.
3. Compact medium fuchsia-pink flowers for a long period in summer.

BRIEF DESCRIPTION OF THE DRAWINGS

The photographs of the new plant demonstrate the unique traits of 'Pardon My Pink' and the overall appearance of the plant at two-years old in the full sun trial garden of a nursery in Zeeland, Mich. The colors are as accurate as reasonably possible with color reproductions. Variation in ambient light spectrum, source and direction may cause the appearance of minor variation in color.

FIG. 1 shows the new plant in flower.

DETAILED BOTANICAL DESCRIPTION

The following descriptions and color references are based on the 2001 edition of The Royal Horticultural Society Colour Chart except where common dictionary terms are used. *Monarda didyma* 'Pardon My Pink' has not been observed under all possible environments. The phenotype may vary slightly with different growing environments such as temperature, light, fertility, soil pH, moisture and maturity levels, but without any change in the genotype. The following observations and size descriptions are based on two-year old greenhouse-grown plants in gallon containers at a nursery in Zeeland, Mich. with supplemental fertilizer and water as needed but without plant growth regulators or pinching.

Botanical classification: *Monarda didyma.*

Parentage: Female (seed) parent is *Monarda didyma* 'ACrade' U.S. Plant Pat. No. 19,580; male (pollen) parent is *Monarda didyma* 'AChall' U.S. Plant Pat. No. 19,582.

Plant habit: Hardy herbaceous perennial, compact, producing several stems spreading by rhizomes; 24 to 28 cm tall at flowering and 35 to 50 cm wide; flowering begins mid-summer in Michigan and continuing for about 5 to 8 weeks.

Propagation: Stem cuttings.

Time to produce finished crop in 3.8 liter pots: About 8 to 10 weeks; moderate rate of growth.

Root: Fine, fibrous and freely branching; color creamy white to tan depending on soil type.

Leaves: Simple, lanceolate, opposite, serrated, puberulent above and below; lustrous above, semi-lustrous to matte below; acute apex, ovate to rounded base; 4.5 to 8.0 cm long by 3.0 to 3.5 cm wide, average about 7.0 cm long and 3.2 cm wide; young leaves nearest RHS 137C on top, between RHS 146B and RHS 138B below; older leaves between RHS 139A and RHS 137A.

Foliage fragrance: Pleasantly lemony.

Veins: Pinnate; pubescent below with minute puberulent above, slightly sunken above and raised below.

Vein color: Above midrib nearest RHS 138C, center portion of lateral veins nearest RHS 135A above with distal vein portion nearest RHS 137A; underneath midrib between RHS 147C and RHS 147D with lateral veins nearest RHS 147C blending to between RHS 146B and RHS 138B on perimeter.

Petiole: Pubescent, slightly concaved above, about 10.0 mm long and 2.0 mm across; nearest RHS 147D above and nearest RHS 147C underneath.

Stems: Squared, puberulent, densely pubescent at nodes; about 3.0 mm across; nearest RHS 146B in upper portion with base portion between RHS N187C and RHS N187B.

Flowers: Single labiate flowers arranged in terminal globular head about 7.0 cm across and 4.0 cm tall opening from the center and progressing outwardly and down; persisting about 5 days in Michigan; numerous, about 200 flowers per head.

Flower fragrance: Moderately spicy.

Buds one to two days prior to opening: Narrowly oblanceolate, curved downward; about 2.2 cm long and 3 mm diameter; nearest RHS 61C in distal one third with a lighter base of white, lighter than RHS N155D or RHS 155D; younger bud color when just protruding beyond sepals apex nearest RHS 145D.

Petals: Labiate, curved downward; split in two in the distal 1.2 cm with upper lip fused into a hood about 3.0 cm long and 2.5 mm diameter; lower lip about 3.5 cm long comprising three lobes including two side lobes about 1.0 mm long with rounded apex and center lobe about 4.0 to 5.0 mm long split in the distal 1.0 mm; both lobes glandular and pubescent outer surfaces with fine hairs the same color as petals; both lobes glabrous on inner surfaces; self-cleaning.

Petal color: Color of all petals on both surfaces nearest RHS 61B with basal 5.0 mm white, lighter than RHS 155D or RHS N155D.

Filaments: Two, about 3.2 cm long by 0.5 mm diameter; lighter than RHS N66D.

Anther: Oblong elliptic, dorsifixed, longitudinal; 2.2 mm by 1.0 mm nearest RHS 158A with longitudinal dehiscence line nearest RHS 187A.

Pollen: Abundant, elliptic to globose, less than 0.1 mm;. nearest RHS 15D.

Pistil: One per flower.

Style: About 3.8 cm by 0.25 mm; nearest RHS N155D with tinting increasing at distal end to nearest RHS 61B.

Stigma: Split in two in the distal 2.0 mm, 0.25 mm in diameter; RHS 64A.

Ovary: 1.0 mm by 0.75 mm, between RHS 143D and RHS 144B.

Sepals: Five, apiculate apex, base fused forming corolla about 9.0 mm long and 2.0 mm diameter; apex glandular and with minute hairs on outer surface; sepal apical margin color nearest RHS 183A, distal two thirds of outer corolla surface nearest RHS 138C with darker veins of RHS 138A; proximal half of outer corolla surface lighter than RHS 145D without stripes; inner surfaces same color as outer.

Peduncle: Pubescent, stiff, strong, erect, squared to about 0.4 cm across and 25 cm long; nearest RHS 138A; about 25 per plant; naturally branched at nodes; average 2.0 cm between nodes; 11 to 13 nodes per stem.

Fruit: Single nutlet, elliptical, about 1.0 mm long and 0.7 mm wide.

Hardiness: The new plant grows best with plenty of moisture and adequate drainage; hardy to at least from USDA zone 4 through 8.

Disease and pest resistance: Demonstrated powdery mildew resistance in side by side comparison at least equal that of 'ACrade' and better than 'AChall' and 'Pink Lace' U.S. Plant Pat. No. 18,367.

I claim:

1. A new and distinct cultivar of ornamental Bee Balm plant, *Monarda didyma* 'Pardon My Pink', as herein described and illustrated, with very short compact habit, medium to dark green foliage, numerous medium fuchsia-pink flowers and resistance to powdery mildew especially suitable as a potted plant, for the garden, patio, and for cut flower arrangements.

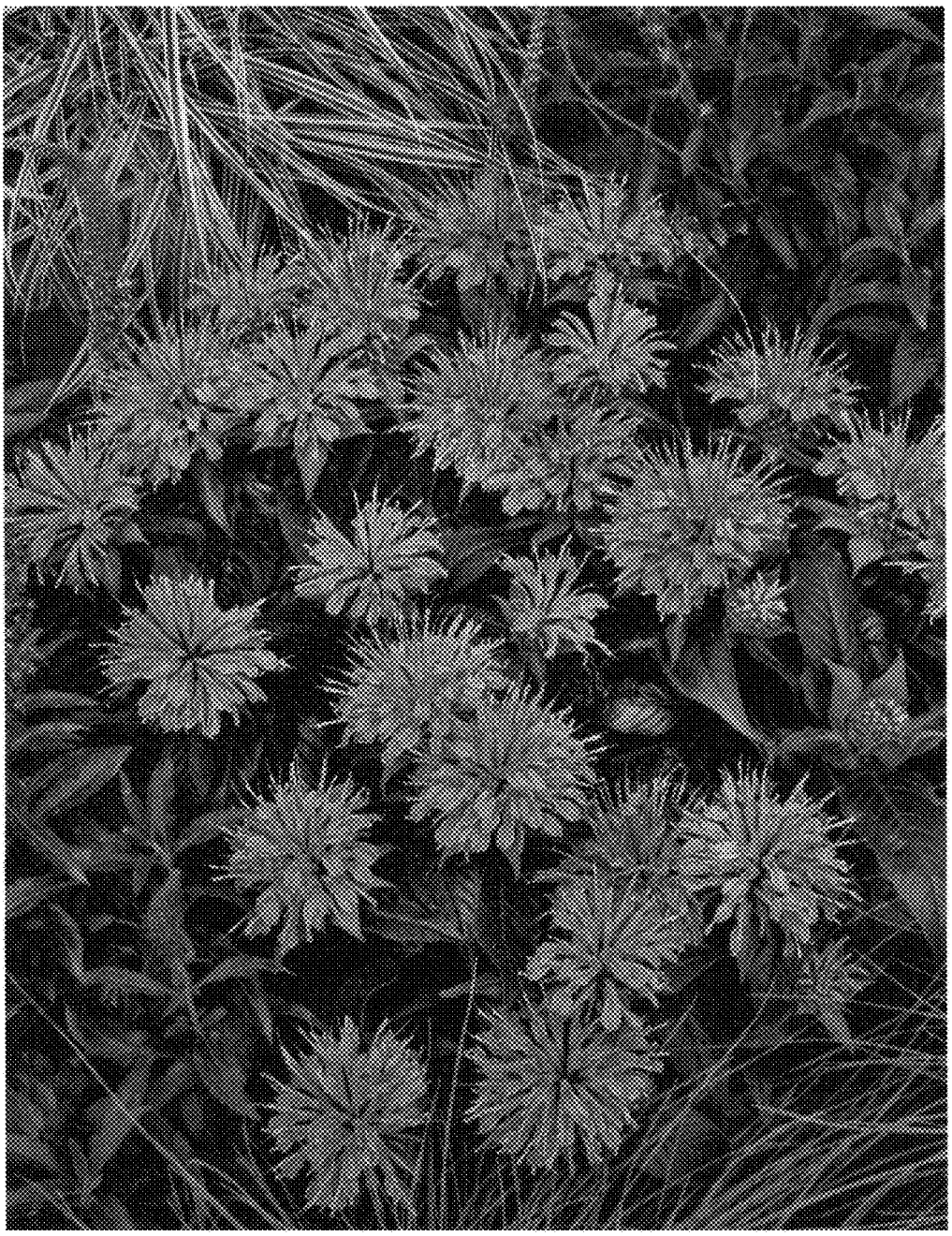

* * * * *